United States Patent [19]

Mark et al.

[11] Patent Number: 4,758,428

[45] Date of Patent: Jul. 19, 1988

[54] MULTICLASS HYBRID INTERFERONS

[75] Inventors: David F. Mark, Hercules; Abla A. Creasey, San Mateo, both of Calif.

[73] Assignee: Cetus Corporation, Emeryville, Calif.

[21] Appl. No.: 755,265

[22] Filed: Jul. 15, 1985

Related U.S. Application Data

[60] Division of Ser. No. 463,574, Feb. 3, 1983, Pat. No. 4,569,908, which is a continuation-in-part of Ser. No. 340,782, Jan. 19, 1982, abandoned.

[30] Foreign Application Priority Data

Jan. 19, 1983 [CA] Canada ................................. 419758

[51] Int. Cl.⁴ ..................... A61K 45/02; C07K 13/00; C07K 15/26; C12P 21/00
[52] U.S. Cl. ..................................... 424/85; 530/351; 435/68; 435/811
[58] Field of Search .................. 424/85; 530/351; 435/68, 172.3, 811

[56] References Cited

U.S. PATENT DOCUMENTS 4,678,751  7/1987  Goeddel ............................ 435/811

OTHER PUBLICATIONS

Shepard et al., Nature, vol. 294, pp. 563–565, 1981.

Primary Examiner—Blondel Hazel
Attorney, Agent, or Firm—Janet E. Hasak; Albert P. Halluin

[57] ABSTRACT

New multiclass hybrid interferon polypeptides, their corresponding encoding recombinant DNA molecules and transformed hosts which produce the new interferons are described. The amino acid sequences of these hybrids include at least two different subsequences, one of which has substantial homology with a portion of a first class of interferon (e.g., HuIFN-α) and the other which has substantial homology with a portion of a second class of interferon (e.g., HuIFN-β). Data indicates the interferon activity of α-β hybrids may be substantially restricted to either cell growth regulatory activity or antiviral activity.

9 Claims, 14 Drawing Sheets

COMPARISON OF IFN AMINO ACID SEQUENCE/

```
                10        20        30        40        50
                |         |         |         |         |
IFN-α  A    CDLPQTHSLGSRRTLMLLAQMRKISLFSCLKDRHDFGFPQEEF-GNQFQKAETIP
       B    CDLPQTHSLGNRRALILLAQMRRISPFSCLKDRHDFEFPQEEFDDKDFQKAQAIS
       C    CDLPQTHSLGNRRALILLGQMGRISPFSCLKDRHDFRIPQEEFDGNQFQKAQAIS
       D    CDLPETHSLDNRRTLMLLAQMSRISPSSCLMDRHDFGFPQEEFDGNQFQKAPAIS
       E    CDLPQAHSVGNRRAFILLTQMRRISPFSYLKDRHDFDFPHQVFHGMHFQKVQAIF
       F    CDLPQTHSLGNRRALILLAQMGRISPFSCLKDRHDFGFPQEEFDGNQFQKAQAIS
       G                            HDFGFPQEEFDGNQFQKAQAIS
       H    CNLSQTHSLNNRRTLMLMAQMRRISPFSCLKDRHDFEFPQEEFDGNQFQKAQAIS
      61A   MCDLPQTHSLSNRRTLMIMAQMGRISPFSCLKDRHDFGFPQEEFDGNQFQKAQAIS

IFN-β 1     MSYNLLGFLQRSSNFQCQKLLWQ LNGRLEYCLKDRMNFDIPEEIKQLQQFQKEDAAL
```

```
                60        70        80        90       100       110
                |         |         |         |         |         |
IFN-α  A    VLHEMIQQIFNLFSTKDSSAAWDETLLDKFYTELYQQLNDLEACVIQGVGVTETP
       B    VLHEMIQQTFNLFSTKDSSAALDETLLDEFYIELDQQLNDLEVLCDQEVGVLESP
       C    VLHEMIQQTFNLFSTEDSSAAWEQSLLEKFSTELYQQLNDLEACVIQEVGVEETP
       D    VLHELIQQIFNLFTTKDSSAAWDEDLLDKFCTELYQQLNDLEACVMQEERVGETP
       E    LFHEMIQQTFNLFSTKDSSDTWDETLLDKSYTELYQQLNDLEACVM*KVGVEETP
       F    VLHEMIQQTFNLFSTKDSSATWEQSLLEKFSTELNQQLNDLEACVIQEVGVEETP
       G    VLHEMIQQTFNLFSTKDSSATWDETLLDKFYTELYQQLNDLEACMMQEVGVEDTP
       H    VLHEMIQQTFNLFSTKNSSAAWDETLLEKFYIELFQQIRDLEACVIQEVGVEETP
      61A   VLHEMIQQTFNLFSTKDSSATWDETLLDKFYTELYQQLNDLEACMMQEVGVEDTP

IFN-β 1     TIYEMLQNIFAIFRQDSSSTGWNETIVENLLANVYHQINHLKTVLEEKLEKEDFT
```

```
                120       130       140       150       160   166
                |         |         |         |         |     |
IFN-α  A    LMKEDSILAVRKYFQRITLYLKEKKYSPCAWEVVRAEIMRSFSLSTNLQESLRSKE
       B    LMYEDSILAVRKYFQRITLYLTEKKYSPCAWEVVRAEIMRSFSLSINLQKRLKSKE
       C    LMKEDSILAVRKYFQRITLYLIEKKYSPCAWEVVRAEIMRSLSFSTNLQKRLRRKD
       D    LMKVDSILAVKKYFRRITLYLTEKKYSPCAWEVVRAEIMRSLSLSTNLQERLRRKE
       E    LRKVDSILAVRKYFQRITLYLKKKYSPCSWEAVRAEIMRSFSL*TNLQERLRRKE
       F    LMKVDSILAVKKYFQRITLYLTEKKYSPCAWEVVRAEIMRSFSLSKIFQERLRRKE
       G    LMKVDSILTVRKYFQRITLYLTEKKYSPCAWEVVRAEIMRSFSLSANLQERLRRKE
       H    LMKEDSILAVRKYFQRITLYLMEKKYSPCAWEVVRAEIMRSFSFSTNLQKRLRRKD
      61A   LMNVDSILTVRKYFQRITLYLTEKKYSPCAWEVVRAEIMRSFSLSANLQERLRRKE

IFN-β 1     RGKLMSSLHLKRYYGRILHYLKAKEYSHCAWTIVRVEILRNFYFINRLTGYLRN
```

FIG. 1

1
ATG TGT GAT CTC CCT GAG ACC CAC AGC CTG GAT AAC AGG AGG ACC TTG ATG CTC CTG GCA
met cys asp leu pro glu thr his ser leu asp asn arg arg thr leu met leu leu ala 61
CAA ATG AGC AGA ATC TCT CCT TCC TCC TGT CTG ATG GAC AGA CAT GAC TTT GGA TTT CCC
gln met ser arg ile ser pro ser ser cys leu met asp arg his asp phe gly phe pro 121
CAG GAG GAG TTT GAT GGC AAC CAG TTC CAG AAG GCT CCA GCC ATC TCT GTC CTC CAT GAG
gln glu glu phe asp gly asn gln phe gln lys ala pro ala ile ser val leu his glu 181
CTG ATC CAG CAG ATC TTC AAC CTC TTT ACC ACA AAA GAT TCA TCT GCT GCT TGG GAT GAG
leu ile gln gln ile phe asn leu phe thr thr lys asp ser ser ala ala trp asp glu 241
GAC CTC CTA GAC AAA TTC TGC ACC GAA CTC TAC CAG CAG CTG AAT GAC TTG GAA GCC TGT
asp leu leu asp lys phe cys thr glu leu tyr gln gln leu asn asp leu glu ala cys 301
GTG ATG CAG GAG GAG AGG GTG GGA GAA ACT CCC CTG ATG AAT GTG GAC TCC ATC TTG GCT
val met gln glu glu arg val gly glu thr pro leu met asn val asp ser ile leu ala 361
GTG AAG AAA TAC TTC CGA AGA ATC ACT CTC TAT CTG ACA GAG AAG AAA TAC AGC CCT TGT
val lys lys tyr phe arg arg ile thr leu tyr leu thr glu lys lys tyr ser pro cys 421
GCC TGG GAG GTT GTC AGA GCA GAA ATC ATG AGA TCC CTC TCT TTA TCA ACA AAC TTG CAA
ala trp glu val val arg ala glu ile met arg ser leu ser leu ser thr asn leu gln 481
GAA AGA TTA AGG AGG AAG GAA TAA TAT CTG GTC AAC ATG AAA CAA TCT TAT TGA CTC
glu arg leu arg arg lys glu ***

541
ATA CAC CAG GTC ACG CTT TCA TGA ATT C

FIG. 3

```
1
ATG AGC TAC AAC TTG CTT GGA TTC CTA CAA AGA AGC AGC AAT TTT CAG TGT CAG AAG CTC
met ser tyr asn leu leu gly phe leu gln arg ser ser asn phe gln cys gln lys leu 61
CTG TGG CAA TTG AAT GGG AGG CTT GAA TAT TGC CTC AAG GAC AGG ATG AAC TTT GAC ATC
leu trp gln leu asn gly arg leu glu tyr cys leu lys asp arg met asn phe asp ile 121
CCT GAG GAG ATT AAG CAG CTG CAG CAG TTC CAC AAG GAG GAC GCC GCA TTG ACC ATC TAT
pro glu glu ile lys gln leu gln gln phe gln lys glu asp ala ala leu thr ile tyr 181
GAG ATG CTC CAG AAC ATC TTT GCT ATT TTC AGA CAA GAT TCA TCT AGC ACT GGC TGG AAT
glu met leu gln asn ile phe ala ile phe arg gln asp ser ser ser thr gly trp asn 241
GAG ACT ATT GTT GAG AAC CTC CTG GCT AAT GTC TAT CAT CAG ATA AAC CAT CTG AAG ACA
glu thr ile val glu asn leu leu ala asn val tyr his gln ile asn his leu lys thr 301
GTC CTG GAA GAA AAA CTG GAG AAA GAA GAT TTC ACC AGG GGA AAA CTC ATG AGC AGT CTG
val leu glu glu lys leu glu lys glu asp phe thr arg gly lys leu met ser ser leu 361
CAC CTG AAA AGA TAT TAT GGG AGG ATT CTG CAT TAC CTG AAG GCC AAG GAG TAC AGT CAC
his leu lys arg tyr tyr gly arg ile leu his tyr leu lys ala lys glu tyr ser his 421
TGT GCC TGG ACC ATA GTC AGA GTG GAA ATC CTA AGG AAC TTT TAC TTC ATT AAC AGA CTT
cys ala trp thr ile val arg val glu ile leu arg asn phe tyr phe ile asn arg leu 481
ACA GGT TAC CTC CGA AAC TGA AGA TC
thr gly tyr leu arg asn ***
```

FIG. 5

```
                                                    HinfI
                                         70          ↓
Alpha-1. 5'...ATC TTC AAC CTC TTT ACC ACA AAA GAT TCA TCT GCT.....3'
             ile phe asn leu phe thr thr lys asp ser ser ala
             ile phe ala ile phe arg gln asp ser ser ser thr
Beta-1.  5'...ATC TTT GCT ATT TTC AGA CAA GAT TCA TCT AGC ACT.....3'
                             70          ↑
                                       HinfI
```
FIG. 6
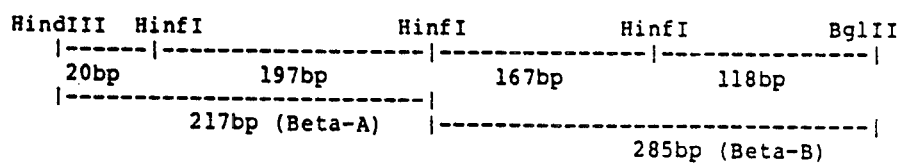
FIG. 7
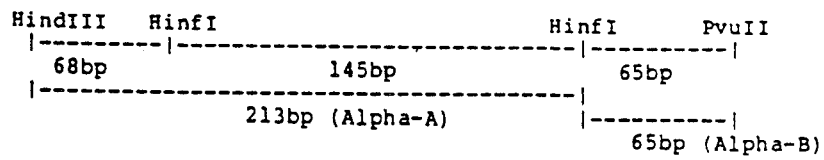
FIG. 8

Hind III

```
1
ATG TGT GAT CTC CCT GAG ACC CAC AGC CTG GAT AAC AGG AGG ACC TTG ATG CTC CTG GCA
met cys asp leu pro glu thr his ser leu asp asn arg arg thr leu met leu leu ala 61
CAA ATG AGC AGA ATC TCT CCT TCC TCC TGT CTG ATG GAC AGA CAT GAC TTT GGA TTT CCC
gln met ser arg ile ser pro ser ser cys leu met asp arg his asp phe gly phe pro 121
CAG GAG GAG TTT GAT GGC AAC CAG TTC CAG AAG GCT CCA GCC ATC TCT GTC CTC CAT GAG
gln glu glu phe asp gly asn gln phe gln lys ala pro ala ile ser val leu his glu 181
CTG ATC CAG CAG ATC TTC AAC CTC TTT ACC ACA AAA GAT TCA TCT AGC ACT GGC TGG AAT
leu ile gln gln ile phe asn leu phe thr thr lys asp ser ser ser thr gly trp asn 241
GAG ACT ATT GTT GAG AAC CTC CTG GCT AAT GTC TAT CAT CAG ATA AAC CAT CTG AAG ACA
glu thr ile val glu asn leu leu ala asn val tyr his gln ile asn his leu lys thr 301
GTC CTG GAA GAA AAA CTG GAG AAA GAA GAT TTC ACC AGG GGA AAA CTC ATG AGC AGT CTG
val leu glu glu lys leu glu lys glu asp phe thr arg gly lys leu met ser ser leu 361
CAC CTG AAA AGA TAT TAT GGG AGG ATT CTG CAT TAC CTG AAG GCC AAG GAG TAC AGT CAC
his leu lys arg tyr tyr gly arg ile leu his tyr leu lys ala lys glu tyr ser his 421
TGT GCC TGG ACC ATA GTC AGA GTG GAA ATC CTA AGG AAC TTT TAC TTC ATT AAC AGA CTT
cys ala trp thr ile val arg val glu ile leu arg asn phe tyr phe ile asn arg leu 481
ACA GGT TAC CTC CGA AAC TGA AGA TC
thr gly tyr leu arg asn ***
```

FIG. 11

```
1
ATG AGC TAC AAC TTG CTT GGA TTC CTA CAA AGA AGC AGC AAT TTT CAG TGT CAG AAG CTC
met ser tyr asn leu leu gly phe leu gln arg ser ser asn phe gln cys gln lys leu 61
CTG TGG CAA TTG AAT GGG AGG CTT GAA TAT TGC CTC AAG GAC AGG ATG AAC TTT GAC ATC
leu trp gln leu asn gly arg leu glu tyr cys leu lys asp arg met asn phe asp ile 121
CCT GAG GAG ATT AAG CAG CTG CAG CAG TTC CAG AAG GAG GAC GCC GCA TTG ACC ATC TAT
pro glu glu ile lys gln leu gln gln phe gln lys glu asp ala ala leu thr ile tyr 181
GAG ATG CTC CAG AAC ATC TTT GCT ATT TTC AGA CAA GAT TCA TCT GCT GCT TGG GAT GAG
glu met leu gln asn ile phe ala ile phe arg gln asp ser ser ala ala trp asp glu 241
GAC CTC CTA GAC AAA TTC TGC ACC GAA CTC TAC CAG CAG CTG AAT GAC TTG GAA GCC TGT
asp leu leu asp lys phe cys thr glu leu tyr gln gln leu asn asp leu glu ala cys 301
GTG ATG CAG GAG GAG AGG GTG GGA GAA ACT CCC CTG ATG AAT GTG GAC TCC ATC TTG GCT
val met gln glu glu arg val gly glu thr pro leu met asn val asp ser ile leu ala 361
GTG AAG AAA TAC TTC CGA AGA ATC ACT CTC TAT CTG ACA GAG AAG AAA TAC AGC CCT TGT
val lys lys tyr phe arg arg ile thr leu tyr leu thr glu lys lys tyr ser pro cys 421
GCC TGG GAG GTT GTC AGA GCA GAA ATC ATG AGA TCC CTC TCT TTA TCA ACA AAC TTG CAA
ala trp glu val val arg ala glu ile met arg ser leu ser leu ser thr asn leu gln 481
GAA AGA TTA AGG AGG AAG GAA TAA TAT CTG GTC AA CAT GAA AAC AAT TCT TAT TGA CTC
glu arg leu arg arg lys glu ***

541
ATA CAC CAG GTC ACG CTT TCA TGA ATT C
```

FIG. 14

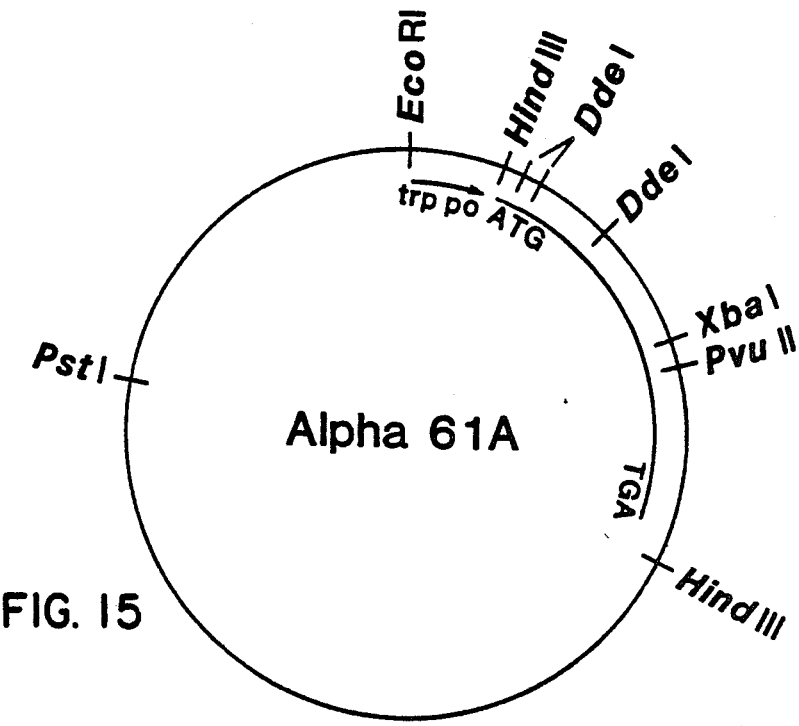

FIG. 15

```
1
GAA TTC CGA CAT CAT AAC GGT TCT GGC AAA TAT TCT GAA ATG AGC TGT TGA CAA TTA ATC
Eco RI

61                                                                    Met Cys
ATC GAA CTA GTT AAC TAG TAC GCA AGT TCA CGT AAA AAG GGT ATC GAT AAG CTT ATG TGT

121
Asp Leu Pro Gln Thr His Ser Leu Ser Asn Arg Arg Thr Leu Met Ile Met Ala Gln Met
GAT CTG CCT CAG ACC CAC AGC CTG AGT AAC AGG AGG ACT TTG ATG ATA ATG GCA CAA ATG
Sau 3A

181
Gly Arg Ile Ser Pro Phe Ser Cys Leu Lys Asp Arg His Asp Phe Gly Phe Pro Gln Glu
GGA AGA ATC TCT CCT TTC TCC TGC CTG AAG GAC AGA CAT GAC TTT GGA TTT CCT CAG GAG

241
Glu Phe Asp Gly Asn Gln Phe Gln Lys Ala Gln Ala Ile Ser Val Leu His Glu Met Ile
GAG TTT GAT GGC AAC CAG TTC CAG AAG GCT CAA GCC ATC TCT GTC CTC CAT GAG ATG ATC

301
Gln Gln Thr Phe Asn Leu Phe Ser Thr Lys Asp Ser Ser Ala Thr Trp Asp Glu Thr Leu
CAG CAG ACC TTC AAT CTC TTC AGC ACA AAG GAC TCA TCT GCT ACT TGG GAT GAG ACA CTT

361
Leu Asp Lys Phe Tyr Thr Glu Leu Tyr Gln Gln Leu Asn Asp Leu Glu Ala Cys Met Met
CTA GAC AAA TTC TAC ACT GAA CTT TAC CAG CAG CTG AAT GAC CTG GAA GCC TGT ATG ATG

421
Gln Glu Val Gly Val Glu Asp Thr Pro Leu Met Asn Val Asp Ser Ile Leu Thr Val Arg
CAG GAG GTT GGA GTG GAA GAC ACT CCT CTG ATG AAT GTG GAC TCT ATC CTG ACT GTG AGA

481
Lys Tyr Phe Gln Arg Ile Thr Leu Tyr Leu Thr Glu Lys Lys Tyr Ser Pro Cys Ala Trp
AAA TAC TTT CAA AGA ATC ACT CTC TAT CTG ACA GAG AAG AAA TAC AGC CCT TGT GCA TGG

541
Glu Val Val Arg Ala Glu Ile Met Arg Ser Phe Ser Leu Ser Ala Asn Leu Gln Glu Arg
GAG GTT GTC AGA GCA GAA ATC ATG AGA TCC TTC TCT TTA TCA GCA AAC TTG CAA GAA AGA

601
Leu Arg Arg Lys Glu ***
TTA AGG AGG AAG GAA TGA AAA CTG GTT CAA CAT CGA AAT GAT TCT CAT TGA CTA GTA CAC

661
ATA AGC TT
Hind III
```

FIG. 16

```
                                          DdeI
                                         ↓ 40
ALPHA-61A  5'....CAT GAC TTT GGA TTT CCT CAG GAG GAG TTT GAT GGC....3'
                 His Asp Phe Gly Phe Pro Gln Glu Glu Phe Asp Gly

Met Asn Phe Asp Ile Pro Glu Glu Ile Lys Gln Leu
BETA-1     5'....ATG AAC TTT GAC ATC CCT GAG GAG ATT AAG CAG CTG....3'
                                  40   ↑
                                      DdeI
```

FIG. 17

```
EcoRI          HindIII DdeI                 DdeI                   XbaI    PvuII
|---------------|---|--|------------------|----------------------|-------|
                    |------120 bp--(Alpha)--|
```

FIG. 18

```
EcoRI      DdeI           DdeI BglII   DdeI DdeI                        BamHI
|----------|---------------|---|-------|---|--------------------------|
           |-----381 bp--(Beta)--|
```

FIG. 19

```
HindIII DdeI 91 bp  DdeI              329 bp            DdeI    XhoII
|---|--|-----------|----------------------------------|---------|
```

FIG. 22

```
1
ATG TGT GAT CTG CCT CAG ACC CAC AGC CTG AGT AAC AGG AGG ACT TTG ATG ATA ATG GCA
met cys asp leu pro gln thr his ser leu ser asn arg arg thr leu met ile met ala 61
CAA ATG GGA AGA ATC TCT CCT TTC TCC TGC CTG AAG GAC AGA CAT GAC TTT GGA TTT CCT
gln met gly arg ile ser pro phe ser cys leu lys asp arg his asp phe gly phe pro 121
CAG CTG CAG CAG TTC CAG AAG GAG GAC GCC GCA TTG ACC ATC TAT GAG ATG CTC CAG AAC
gln leu gln gln phe gln lys glu asp ala ala leu thr ile tyr glu met leu gln asn 181
ATC TTT GCT ATT TTC AGA CAA GAT TCA TCT AGC ACT GGC TGG AAT GAG ACT ATT GTT GAG
ile phe ala ile phe arg gln asp ser ser ser thr gly trp asn glu thr ile val glu 241
AAC CTC CTG GCT AAT GTC TAT CAT CAG ATA AAC CAT CTG AAG ACA GTC CTG GAA GAA AAA
asn leu leu ala asn val tyr his gln ile asn his leu lys thr val leu glu glu lys 301
CTG GAG AAA GAA GAT TTC ACC AGG GGA AAA CTC ATG AGC AGT CTG CAC CTG AAA AGA TAT
leu glu lys glu asp phe thr arg gly lys leu met ser ser leu his leu lys arg tyr 361
TAT GGG AGG ATT CTG CAT TAC CTG AAG GCC AAG GAG TAC AGT CAC TGT GCC TGG ACC ATA
tyr gly arg ile leu his tyr leu lys ala lys glu tyr ser his cys ala trp thr ile 421
GTC AGA GTG GAA ATC CTA AGG AAC TTT TAC TTC ATT AAC AGA CTT ACA GGT TAC CTC CGA
val arg val glu ile leu arg asn phe tyr phe ile asn arg leu thr gly tyr leu arg 481
AAC TGA
asn ***
```

FIG. 23

MULTICLASS HYBRID INTERFERONS

This application is a divisional application of U.S. application Ser. No. 463,574 filed Feb. 3, 1983, now issued as U.S. Pat. No. 4,569,908 on Feb 11, 1986, which is a continuation-in-part application of U.S. application Ser. No. 340,782, filed Jan. 19, 1982, now abandoned.

DESCRIPTION

1. Technical Field

This invention is in the field of biotechnology. More particularly it relates to multiclass hybrid interferon polypeptides, recombinant DNA that codes for the polypeptides, recombinant vectors that include the DNA, host organisms transformed with the recombinant vectors that produce the polypeptides, methods for producing the hybrid interferon polypeptides, pharmaceutical compositions containing the polypeptides, and therapeutic methods employing the polypeptides.

2. Background Art

Since the discovery by Isaacs and Lindenmann of interferon in 1957, many investigations have been conducted on the efficacy of interferon for treating various human diseases. Interferon is now generally thought to have three major clinically advantageous activities normally associated with it, namely, antiviral activity (Lebleu et al, *PNAS USA*, 73:3107–3111 (1976)), cell (including tumor) growth regulatory activity (Gresser et al, *Nature*, 251:543–545 (1974)), and immune regulatory activity (Johnson, *Texas Reports Biol Med*, 35:357–369 (1977)).

Interferons are produced by most vertebrates in the presence of certain inducers including viruses. Human interferons (HuIFN) thus far discovered have been divided into three classes: $\alpha$, $\beta$, and $\gamma$. HuIFN-$\alpha$ is produced in human leukocyte cells or in transformed leukocyte cell lines known as lymphoblastoid lines. HuIFN-$\alpha$ has been purified to homogeneity (M. Rubenstein et al, "Human Leukocyte Interferon: Production, Purification to Homogeneity and Initial Characterization", *PNAS*, 76:640–44 (1979)). The pure product is heterogeneous in size and the various molecular species seem to have differences in crossspecies antiviral activities (L.S. Lin et al "Characterization of the Heterogeneous Molecules of Human Interferons: Differences in cross-species antiviral activities of various molecular populations in human leukocyte interferons", *J Gen Virol* 39:125–130 (1978)). The heterogeneity of the leukocyte interferon has subsequently been confirmed by the molecular cloning of a family of closely related HuIFN-$\alpha$ genes from human leukocyte cells and from lymphoblastoid cell lines (S. Nagata et al, "The structure of one of the eight or more distinct chromosomal genes for human interferon-$\alpha$", *Nature*, 287:401–408 (1980); D.V. Goeddel et al, "The structure of eight distinct cloned human leukocyte interferon cDNAs", *Nature*, 290:20–26 (1981)). However, a comparison of the DNA and amino acid sequences of the HuIFN-$\alpha$ interferons also reveals that many of the sequences exhibit homology at the nucleotide level, some in the order of 70 percent, and that the related gene products of these homologous DNA sequences are also homologous. (D. V. Goeddel et al, "The structure of eight distinct cloned human leukocyte interferon cDNAs", *Nature*, 290:20–26 (1981); N. Mantein et al, "The nucleotide sequence of a cloned human leukocyte interferon cDNA", *Gene*, 10:1–10 (1980); M. Streuli et al, "At least three human type $\alpha$ interferons: Structure of $\alpha$-2", *Science*, 209:1343–1347 (1980)).

HuIFN-$\beta$ is produced in human fibroblast cells. Although there is evidence that human fibroblast cells may be producing more than one HuIFN-$\beta$ (P. B. Sehgal and A. D. Sagar, "Heterogeneity of Poly(I) and Poly(C) induced human fibroblast interferon mRNA species", *Nature*, 288:95–97 (1980)), only one species of HuIFN-$\beta$ has been purified to homogeneity (E. Knight, Jr., "Interferon: Purification and initial characterization from human diploid cells", *PNAS*, 73:520–523 (1976); W. Berthold et al, "Purification and in vitro labeling of interferon from a human fibroblast cell line", *J Biol Chem*, 253:5206–5212 (1978)). The amino terminal sequence of this purified HuIFN-$\beta$ has been determined (E. Knight, Jr. et al, "Human fibroblast interferon: Amino acid analysis and amino terminal amino acid sequence", *Science*, 207:525–526 (1981)). Molecular cloning by recombinant DNA techniques of the gene coding for this interferon has been reported (T. Taniguchi et al, "Construction and Identification of a Bacterial Plasmid Containing the Human Fibroblast Interferon Gene Sequence", *Proc Japan Acad*, 55 Ser B, 464–469 (1979)). This well characterized human fibroblast interferon will be referred to as HuIFN-$\beta$1 in the rest of this specification.

Although interferons were initially identified by their antiviral effects (A. Isaacs and J. Lindenmann, "Virus Interference I. The Interferon", *Proc Royal Soc*, Ser B, 147:258–267 (1957)), the growth regulatory effect of interferons is another biological activity that has also been well documented (I. Gressor and M. G. Tovey, "Antitumor effects of interferon" *Biochim Biophys Acta*, 516:213–247 (1978); W. E. Stewart, "The Interferon System" Springer-Verlag, New York, 292–304 (1979); A. A. Creasey et al, "Role of G0-G1 Arrest in the Inhibition of Tumor Cell Growth by Interferon", *PNAS*, 77:1471–1475 (1980)). In addition, interferon plays a role in the regulation of the immune response (H. M. Johnsons, *Texas Reports on Biology and Medicine*, 35:357–369 (1977)), showing both immunopotentiating and immunosuppressive effects. Interferon may mediate the cellular immune response by stimulating "natural killer" cells in the spontaneous lymphocyte - mediated cytotoxicity (J. Y. Djeu et al, "Augmentation of mouse natural killer cell activity by interferon and interferon inducers", *J Immun*, 122: 175–181 (1979)).

Studies concerning the biological activities of interferons have been conducted by taking advantage of nucleotide and amino acid sequence homologies between HuIFN-$\alpha$1 and HuIFN-$\alpha$2. Hybrids of the two genes were constructed in vitro by recombinant DNA techniques such that the DNA sequence coding for the amino terminus of one gene was fused to the DNA sequence coding for the carboxy terminus of the other gene (M. Streuli et al, "Target cell specificity of two species of human interferon-$\alpha$ produced in *Escherichia coli* and of hybrid molecules derived from them", PNAS 78:2848–2852 (1981); P. K. Weck et al, "Antiviral activities of hybrids of two major human leukocyte interferons", *Nucleic Acids Res*, 9:6153–6166 (1981)).

HuIFN-$\alpha$1 has a lower specific activity on human WISH cells than on bovine MDBK cells while HuIFN-$\alpha$2 behaves in the opposite manner. Also, HuIFN-$\alpha$1 has some activity on mouse L cells while HuIFN-$\alpha$2 has little activity on mouse cells. However, the HuIFN-$\alpha$2-$\alpha$1 hybrid (amino terminal sequence of HuIFN-$\alpha$2 fused to the carboxy terminal sequence of HuIFN-$\alpha$1) has much higher activity on mouse L cells than on human cells (M. Streuli et al, "Target cell specificity of two species of human interferon-α produced in E.coli and of hybrid molecules derived from them", PNAS, 78:2848–2852 (1981); N. Stebbing et al, "Comparison of the biological properties of natural and recombinant DNA derived human interferons", The Biology of the Interferon System, Elsevier/North-Holland, 25–33 (1981); P. K. Weck et al, "Antiviral activities of hybrids of two major leukocyte interferons", Nucleic Acids Res, 9:6153–6166 (1981)). Therefore, target cell specifications can be altered by making hybrid proteins.

Although these α-α hybrids exhibited changes in target cell specificity as compared to the parent, it was not demonstrated that there was any attenuation or any restriction of any of the three interferon activities.

Under some circumstances, the plural biological activity of interferon may be undesirable. For example, in the clinical treatment of patients who have received organ transplants and whose immune system has been suppressed because of anti-rejection drugs, administration of interferon to combat viral infection could result in undesirable stimulation of the immune response system and consequent rejection of the transplanted organs. Moreover, in clinical applications it is generally desirable in principle to focus drug therapy on a particular problem such as viral infection or tumor growth without the possibility of complicating factors resulting from other activities of the administered drug. In such treatment and applications it would be desirable to be able to use an interferon whose activity is limited to the desired activity. The present invention provides a novel group of hybrid interferons that have restricted interferon activity as well as changes in target cell specificity.

DISCLOSURE OF THE INVENTION

One aspect of the invention is a multiclass hybrid interferon polypeptide having an amino acid sequence composed of at least two distinct amino acid subsequences one of which subsequences corresponds substantially in amino acid identity, sequence and number to a portion of a first interferon and the other of which corresponds in amino acid identity, sequence and number to a portion of a second interferon of a different interferon class from the first interferon.

A second aspect of the invention is DNA units or fragments comprising nucleotide sequences that upon expression encode for the above described multiclass hybrid interferons.

A third aspect of the invention is cloning vehicles (vectors) that include the above described DNA.

A fourth aspect of the invention is host organisms or cells transformed with the above described cloning vehicles that produce the above described multiclass hybrid interferons.

A fifth aspect of the invention is processes for producing the above described multiclass hybrid interferons comprising cultivating said transformed host organisms or cells and collecting the multiclass hybrid interferons from the resulting cultures.

Another aspect of the invention is pharmaceutical compositions comprising an effective amount of one or more of the above described multiclass hybrid interferons admixed with a pharmaceutically acceptable carrier.

Another aspect of the invention is a method of regulating cell growth in an animal patient comprising administering to said patient a cell growth regulating amount of one or more of the above described multiclass hybrid interferons having interferon activity substantially restricted to cell growth regulatory activity.

Still another aspect of the invention is a method of treating an animal patient for a viral disease comprising administering to said patient a viral disease inhibiting amount of one or more of the above described multiclass hybrid interferons having interferon activity substantially restricted to antiviral activity.

BRIEF DESCRIPTION OF THE DRAWINGS

FIG. 1 shows the amino acid sequence for several different interferons indicated as β1, αA through αH and α61A with regions of sequence homology being enclosed by dark lines. The one letter abbreviations recommended by the IUPAC-IUB Commission on Biochemical Nomenclature are used; A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

FIG. 3 illustrates the nucleotide sequence between the HindIII site and the EcoRI site of pGW5, as well as the amino acid sequence of HuIFN-α1 which the plasmid expresses.

FIG. 5 illustrates the nucleotide sequence between the HindIII site and the BglII sites of the plasmid pDM101/trp/β1 as well as the amino acid sequence of the expressed HuIFN-β1.

FIG. 6 illustrates the amino acid sequences of HuIFN-α1 and HuIFN-β1 at around amino acid 70 of both proteins.

FIG. 7 illustrates the 217 base pair (bp) HindIII-HinfI fragment and the 285 bp HinfI-BglIII fragment of the HuIFN-β1 gene, as generated in the methodology of the invention.

FIG. 8 illustrates the 213 base pair HindIII-HinfI fragment and the 65 base pair HinfI-PvuII fragment of the HuIFN-α1 gene, as generated in the methodology of the invention.

FIG. 11 illustrates the nucleotide sequence of the region coding for the hybrid protein of Example I, as well as showing the amino acid sequence of the hybrid protein.

FIG. 14 illustrates the nucleotide sequence of the hybrid gene shown in FIG. 13, as well as showing the corresponding amino acid sequence of the hybrid protein expressed by said gene.

FIG. 15 illustrates the structure of plasmid mid pα61A used in the methodology of the invention.

FIG. 16 illustrates the nucleotide sequence of the E.coli trp promoter as well as the nucleotide sequence of the HuIFN-α61A gene including some of the flanking 3' non coding region of the gene which was inserted between the EcoRI and HindIII sites of the plasmid pBW11. The region coding for the HuIFN-α61A gene begins with the ATG codon at position 113 and terminates with the TGA codon at position 614. The corresponding amino acid sequence of the HuIFN-α61A protein is also shown.

FIG. 17 illustrates the nucleotide and amino acid sequences of HuIFN-β1 and HuIFN-α61A at around amino acid 40 of both proteins.

FIG. 18 illustrates the 387 bp EcoRI-PvuII fragment and the 120 bp (Alpha) HindIII-DdeI fragment of the HuIFN-α61 gene, as generated in the methodology of the invention.

FIG. 19 illustrates the 381 bp (Beta) DdeI-BglII fragment of the HuIFN-β1 gene, as generated in the methodology of the invention.

FIG. 22 is the structure of the coding region of the hybrid gene incorporated in the plasmid of FIG. 21.

FIG. 23 illustrates the nucleotide sequence of the region coding for the hybrid protein of Example III, as well as showing the amino acid sequence of the hybrid protein.

MODES FOR CARRYINGOUT THE INVENTION

Figure 2:
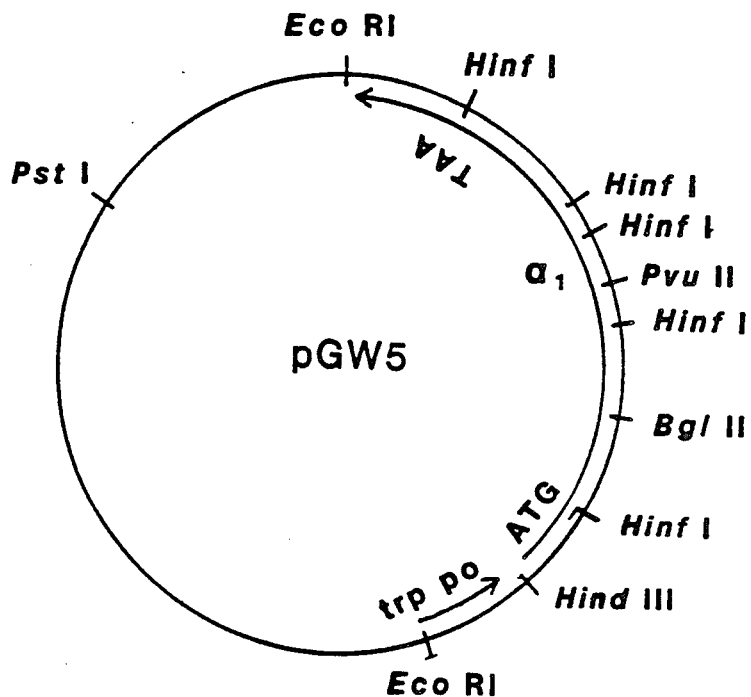
FIG. 2 illustrates the structure of plasmid pGW5 used in the methodology of the invention.

The hybrid interferons of the invention have an amino acid sequence composed of at least two distinct amino acid subsequences that are respectively substantially identical to portions of interferons from different classes. The term "substantially identical" means that a subsequence of the hybrid exhibits at least about 70%, preferably at least about 95%, and most preferably 100% homology with an amino acid subsequence of a given interferon. Lack of complete homology may be attributable to single or multiple base substitutions, deletions, insertions, and site specific mutations in the DNA which on expression code for the hybrid or given interferon amino acid sequences. When the hybrid is composed of more than two subsequences, the additional subsequence(s) may correspond to other portions of the interferons involved in the initial two subsequences (e.g., if the initial two sequences are α1 and β1, the other sequences are α1 or β1 or correspond to portions of interferons different from those involved in the initial two subsequences. Hybrids composed of α interferon and β interferon subsequences are preferred. Hybrids composed only two subsequences (α and β ) are particularly preferred. Individual subsequences will usually be at least about 10 amino acid residues in length, more usually at least about 30 amino acid residues in length.

Multiclass hybrid interferons of the invention exhibit activity that is different from the interferon activity exhibited by the parent interferons of which they are composed. The difference is manifested as a substantial reduction (relative to the parent interferons) or elimination of one or two of the three conventional interferon activities. Preferred hybrids are those whose interferon activity is substantially restricted to one of the three activities. Based on data developed to date the interferon activity of the α-β interferons appears to be substantially restricted to either cell growth regulatory or antiviral activity. In some instances the hybrid interferons also have a host range (target) cell specificity different from that of the parent interferons from which they are derived. In other words hybrid interferons of the invention may exhibit a particular interferon activity in the cells of one but not another animal species in which the parent interferons also exhibit activity.

The structural homologies between different classes of interferons (FIG. 1) permit construction of hybrid DNA molecules coding for the multiclass human hybrid interferon polypeptides. To construct the hybrid gene, it is preferred, although not required, that the gene donating the amino terminal end sequence be fused to some suitable promoter which directs expression of the gene and contains the appropriate promoter, operator and ribosomal binding sequence. The hybrids may be made by selecting suitable common restriction sites within the respective full genes for the different classes of human interferon. As an alternative, different restriction sites may be used for cleavage, followed by repair to blunt ends, followed by blunt end ligation. In either case, the proper reading frame must be preserved. Once the desired segments are ligated together, they are placed in a suitable cloning vector, which is used to transform suitable host organisms or cells. Where the amino terminal fragment carries the promoter, operator and ribosomal binding sequence, expression and biological activity of the resultant hybrids may be directly assayed. Fusions can be directed to different parts of the gene by choosing appropriate restriction enzyme sites.

The following examples further illustrate the invention and are not intended to limit the scope of the invention in any way.

EXAMPLE I

Construction of HuIFN-α1 β1 Hybrid 1

This example describes the construction of a hybrid interferon, containing sequences from HuIFN-α1 and HuIFN-β1. It involves fusing the amino-terminal end coding region of the HuIFN-α1 DNA to the DNA coding for the carboxy-terminal end region of HuIFN-β1 in such a way that the translational reading frame of the two proteins are preserved and the resulting protein being expressed from this hybrid gene will have the amino acid sequence of HuIFN-α1 at its amino terminal portion and the amino acid sequence of HuIFN-β1 at its carboxy terminal portion.

Purification and Isolation of HuIFN-α1 and HuIFN-β1 DNA sequences

The plasmids used in the construction of the HuIFN-α1β1 Hybrid 1 are plasmids pGW5 and pDM101/trp/β1 containing the genes coding for HuIFN-α1 and HuIFN-β1 respectively. The structure of plasmid pGW5 is shown in FIG. 2 and that of plasmid pDM101/trp/β1 in FIG. 4.

The plasmid pGW5 was constructed from the plasmid pBR322 by substituting the region between the EcoRI site to the PvuII site with the E.coli trp promoter and the DNA sequence coding for the mature protein of HuIFN-α1 (FIG. 2). The DNA sequence between the HindIII site and EcoRI site of pGW5, encoding the mature protein of HuIFN-α1, is shown in FIG. 3. Also shown in FIG. 3 is the amino acid sequence of HuIFN-α1 (IFN-αD in FIG. 1). The plasmid pGW5 expressed HuIFN-α1 at high levels in E.coli. When grown in shake-flasks, about 2×10⁶ units of antiviral activity per ml of bacterial culture per A600 can be detected.

Figure 4:
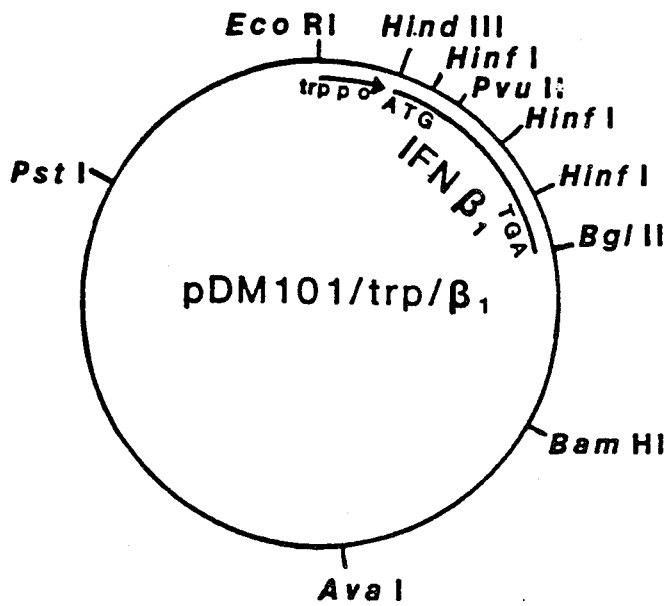
FIG. 4 illustrates the structure of a plasmid pDM101/trp/β1 used in the methodology of the invention.

The plasmid pDM101/trp/β1 is a derivative of pBR322 with the E.coli trp promoter located between the EcoRI and HindIII sites (FIG. 4). The DNA sequences between the HindIII and BglII sites encode the mature HuIFN-β1 protein sequence. The nucleotide sequence together with the amino acid sequence is shown in FIG. 5. When grown in shake-flasks, the E.coli strain carrying pDM101/trp/β1 expresses HuIFN-β1 at a level of 10⁶ units of antiviral activity per ml of bacterial culture per A600.

The hybrid gene was constructed by taking advantage of the homologies between the HuIFN-α1 gene and the HuIFN-β1 gene at around amino acid 70 of both proteins (FIG. 6). There is a HinfI restriction site (GATTC) present within this region of both genes. If both DNA sequences are digested with the enzyme HinfI and the DNA sequence 5'-proximal to the cutting site of the HuIFN-α1 DNA (the arrow in FIG. 6 depicts the cutting site) is ligated to the DNA sequence 3'-proximal to the cutting site of HuIFN-β1, a fusion of the two genes is created while preserving the translational reading frame of both genes.

Since there are several HinfI sites in the coding regions of both HuIFN-α1 and HuIFN-β1, it is not possible to carry out a straightforward exchange of DNA sequences. In the case of HuIFN-β1, a 502 bp HindIII-BglII fragment containing the whole coding region from pDM101/trp/β1 is first isolated. The plasmid DNA was digested with restriction enzymes HindIII and BglII (R. W. Davis et al, "Advanced Bacterial Genetics", Cold Spring Harbor Laboratory, pp. 227-230, 1980). (This reference will be referred to as "Advanced Bacterial Genetics" hereinafter), the DNA fragments were separated on a 1.5% agarose gel in Tris-Borate buffer ("Advanced Bacterial Genetics" p 148) and the DNA fragments visualized by staining with ethidium bromide ("Advanced Bacterial Genetics", pp 153-154). The appropriate DNA fragment, in this case a 502 bp fragment, is cut out of the gel, placed in a dialysis tubing with a minimum amount of 0.1X Tris-Acetate buffer ("Advanced Bacterial Genetics", p 148) and covered with the same buffer in an electroelution box and a voltage of 150-200 volts applied for 1 hour. The DNA is then recovered from the buffer in the dialysis tubing and concentrated by ethanol precipitation. The 502 bp HindIII-BglII fragment was then digested partially with HinfI to obtain the 285 bp partial HinfI fragment (denoted as β-B) coding for the carboxy terminal end of HuIFN-β1 (FIG. 7). The partial digestion of the DNA fragment was accomplished by using one-tenth the amount of restriction enzyme required for complete digestion of the DNA ("Advanced Bacterial Genetics", p 227). The mixture was incubated at the appropriate temperature for the enzyme and aliquots of the digestion mixture were removed at 10-minute intervals for up to 1 hour. The aliquots were then loaded onto a gel and the DNA fragments analyzed. The time point that provides the highest yield of the DNA fragment needed is chosen for a preparative digestion with the restriction enzyme and the appropriate fragment purified from the gel by electroelution. The other HindIII-BglII fragment, (β-C in FIG. 9) consisting of the plasmid pDM101 and trp promoter, is also saved and used in the vector for the HuIFN-α1β1 hybrid.

In the case of HuIFN-α1, pGW5 is digested with HindIII and PvuII and a 278 bp fragment which contains two HinfI sites is purified from the digest. This fragment is then digested partially with HinfI to obtain two fragments, a 213 bp HindIII-HinfI fragment (α-A) and a 65 bp HinfI-PvuII fragment (α-B) (FIG. 8).

Vector Preparation and Selection

Figure 9:
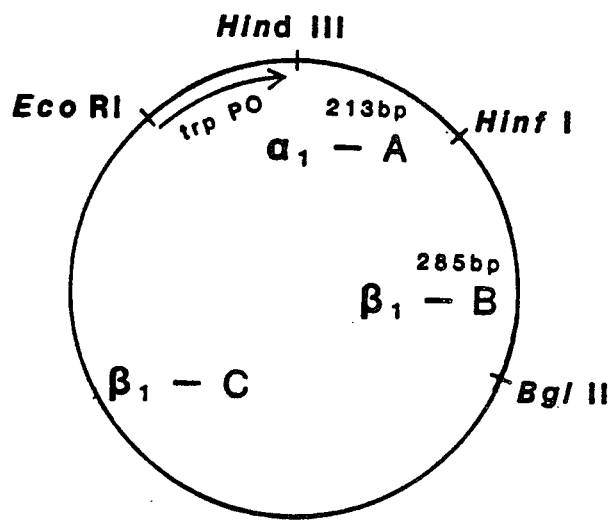
FIG. 9 illustrates the structure of the plasmid coding for the hybrid protein of Example I infra.

Assembly of the plasmid for the direct expressions of the HuIFN-α1 β1 interferon gene can be constructed by ligating fragments α-A, β-B and β-C together as shown in FIG. 9. The ligated DNA was then used to transform competent E.coli cells ("Advanced Bacterial Genetics" pp 140-141). Transformants were plated onto broth plates containing 50 μg per ml of ampicillin and incubated at 37° C. Ampicillin resistant colonies were grown up in rich medium in the presence of 50 μg/ml of ampicillin and plasmid DNA isolated from each individual clone ("Advanced Bacterial Genetics", pp 116-125).

Figure 10:
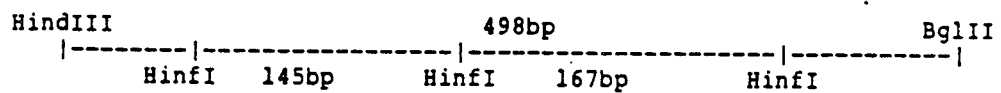
FIG. 10 is the structure of the coding region of the hybrid gene incorporated in the plasmid of FIG. 9.

The gene structure of the desired hybrid clone is shown in FIG. 10. The correct hybrid clone was identified by digesting the plasmid DNA with the restriction enzymes HindIII and BglII and screening for the presence of a 498 bp restriction fragment on 1.5% agarose gel in Tris-Borate buffer ("Advanced Bacterial Genetics", p 148). To further characterize the hybrid clone, the plasmid DNA was digested with HinfI and screened for the presence of the 145 bp and 167 bp restriction fragments. By following this scheme, a number of hybrid clones were identified, one of which (denoted pDM101/trp/hybrid 41) was selected for further characterization and culturing to produce the hybrid interferon.

The nucleotide sequence of the region coding for the hybrid protein is shown in FIG. 11. Also shown in FIG. 11 is the amino acid sequence of the hybrid protein. This hybrid interferon is denoted HuIFN-α1 β1 Hybrid 1 herein. The amino terminal portion of this polypeptide starting with methionine is composed of the amino acid sequence 1-73 of HuIFN-α1 and the carboxy terminal portion is composed of amino acids 74-166 of HuIFN-β1.

The E.coli strain carrying pDM101/trp/hybrid 41 was grown in minimal medium containing 50 μg/ml of ampicillin to express the hybrid protein. The culture was harvested when it reached A600=1.0, concentrated by centrifugation, resuspended in buffer containing 50 mM Tris-HCL pH 8.0, 10 mM ethylenediaminetetraacetic acid (EDTA), 15% sucrose and 1% sodium dodecylsulfate (SDS), and the cells lysed by sonication in a Branson Sonicator. The cell free extract was assayed for (1) inhibiting the growth of transformed cells, (2) activating natural killer cells, and (3) antiviral activity.

Biological Testing of HuIFN-α1 β1 Hybrid 1

(1) Growth Inhibition Assays

Bacterial extracts made from the E.coli strain carrying pDM101/trp/hybrid 41, together with various control extracts, were assayed for their ability to inhibit the growth of two human tumor cell lines, the Daudi line (American Type Culture Collection, Catalog of Cell Strains III, 3rd Edition, Rockville, MD (1979)) and the melanoma line HS294T Clone 6 (A. A. Creasey et al, PNAS, 77:1471-1475, (1980); A. A. Creasey et al, Exp Cell Res, 134:155-160 (1981)).

(a) Inhibition of Growth of Daudi Cells

About $2 \times 10^4$ cells are seeded into each well of a sterile 96-well round bottom microtiter plate. Cells are then incubated overnight at 37° C. Bacterial extracts together with the appropriate controls are added to the cells and then allowed to incubate at 37° C. for three days. On the third day, cells are pulse labeled with 4 μCi well of $^3$H-thymidine for 2-3 hours. The labeling is terminated by addition of 5% trichloroacetic acid (TCA) to precipitate the nucleic acids. The precipitates are filtered and the filters are counted in the scintillation counter. The results for the cells incubated with the bacterial extracts are compared to the results for the controls to obtain a percent inhibition of growth. The results are reported in Table I below.

(b) Inhibition of HS294T Clone 6

About $1.5 \times 10^4$ cells are seeded into each well of a sterile, flexible 48-well flat bottom tissue culture plate. Cells are incubated overnight at 37° C. with 10% $CO_2$.- Bacterial extracts together with various controls are added to the cells and then incubated for three days at 37° C. On the third day, cells are pulse labeled with 2 μCi/well of $^3$H-thymidine for 2-3 hours. The labeling reactions is terminated by addition of cold TCA in 0.3% $Na_4P_2O_7$ (TP). Plates are washed two times with TP solution and three times with cold absolute ethanol, and left to dry at room temperature. A sheet of adhesive tape is stuck to the bottom of the assay plate, securing all the wells in place. The plate is then run through a hot wire cutter. The top of the plate is removed and the individual wells are picked off the adhesive tape and put into scintillation vials containing 5 ml of scintillation fluid and counted in the scintillation counter. Percent growth inhibition was obtained as above. The results are also reported in Table I below.

TABLE I

| HuIFN | U/ml or *dilution of Extract | Percent Inhibition of Growth Cell Lines | |
|---|---|---|---|
| | | Daudi | HS294T Clone 6 |
| $\alpha^1$ | 100 | 70 | 0 |
| | 500 | 80 | 9 |
| $\beta^1$ | 100 | 68 | 43 |
| | 500 | 72 | 80 |
| Hybrid of Example I | *1:2000 | 46 | 4 |
| | *1:20,000 | 24 | 0 |

Note:
Percent inhibition of growth by negative control (pDM101/trp) was included in the calculations to obtain the numbers shown above)

As reported in Table I the hybrid interferon HuIFN-α1 β1 Hybrid 1 inhibited the growth of Daudi cells but it did not inhibit the HS294T Clone 6 cells. Since the HS294T Clone 6 cells are resistant to HuIFN-α1 the hybrid appears to be behaving like HuIFN-α1 in these tests. Therefore, it appears that since the hybrid has the HuIFN-α1 amino terminal sequence as its amino terminus, that portion of the protein may carry the determinant which governs cell specificity.

(2) Stimulation of Natural Killer Cells

Whole blood is obtained from a donor and kept clot-free by adding EDTA. Lymphocytes are separated by centrifugation on a Ficoll/Hypaque gradient. The upper band of lymphocytes is harvested and washed. Interferon samples and various control samples are diluted into 1 ml of Dulbecco's Modified Eagle's Medium (DME) containing 10% fetal calf serum (FCS) and then mixed with 1 ml of lymphocytes ($10^7$ cells) and incubated at 37° C. for 18 hours. The treated lymphocytes are then washed and resuspended in RPMI 1640 medium containing 10% FCS.

Two hours before the lymphocytes are harvested, the target cells (Daudi line) are labeled with $^{51}$Cr by incubating $2 \times 10^6$ Daudi cells with 100 μCi of $^{51}$Cr in 1 ml of RPMI 1640. After two hours, the target cells are washed four times to remove excess label, concentrated by centrifugation and resuspended to $2 \times 10^5$ cells per ml in RPMI 1640. About $2 \times 10^4$ labeled target cells are added to each well of a microtiter plate. Primed lymphocytes together with unprimed controls are added to the target cells in triplicate and incubated for four hours at 37° C. The plate is then centrifuged and 100 μl of media is removed from each well and counted in the gamma counter. Percent killing by the activated natural killer cells is dependent on the interferon concentration. Thus, small amounts of interferon will result in a small percentage of killing and minimal lysis of target cells. By determining the amount of label released into the medium, the amount of natural killer activity can be quantitated. The results of the tests are reported in Table II below.

TABLE II

| ACTIVATION OF NATURAL KILLER CELLS | | |
|---|---|---|
| HuIFN | U/ml or *dilution of extract | Percent Killing (%) |
| $\alpha^1$ | 100 | 39 |
| | 10 | 29 |
| $\beta^1$ | 100 | 38 |
| | 10 | 2 |
| Hybrid of Example I | *1:1000 | 13 |
| Controls: | | |
| pDM101/trp/ Cell Control | *1:1000 | 10 |
| (Spontaneous release of label) | | 7 |

As reported in Table II, the hybrid interferon showed substantially less natural killer activity than HuIFN-β1 and HuIFN-α1.

(3) Antiviral Assays

Interferon antiviral activity in bacterial extracts was determined by comparison with NIH interferon standards using cytopathic effect (CPE) inhibition assays as reviewed previously (W. E. Stewart, "The Interferon System" Springer-Verlag, 17-18, (1979)). The assays were performed on two different cell lines the human trisomic 21 line (GM2504), and the bovine MDBK line, with vesicular stomatitis virus as the challenge virus within the limits of the sensitivity of the CPE inhibition assay ($\geq 30$ U/ml) no antiviral activity in the bacterial extracts containing the hybrid interferon of Example I was detected.

EXAMPLE II

Construction of HuIFN-β1α1 Hybrid1

This example describes the construction of a hybrid interferon containing sequences from HuIFN-α1 and HuIFN-β1. It involves the fusion of the amino terminal coding region of the HuIFN-β1 DNA to the DNA coding for the carboxy terminal region of HuIFN-α1 in such a way that the translational reading frame of the two genes are preserved and the resulting protein being expressed from this hybrid gene will have the amino acid sequence of HuIFN-β1 at its amino terminus and the amino acid sequence of HuIFN-α1 at its carboxy terminus.

Purification and Isolation of HuIFN-α1 and HuIFN-β1 DNA Sequences.

The plasmids used in the construction of HuIFN-β1α1 hybrid 1 are plasmids pGW5 and pDM101/trp/β1 as set forth in Example I.

As in Example I, the hybrid gene of this example was constructed by taking advantage of the homologies between HuIFN-α1 and HuIFN-β1 at around amino acid 70 of both proteins (FIG. 6). The DNA sequence 5'-proximal to the cutting site of the HuIFNβ1 DNA (the arrow in FIG. 6 depicts the cutting site), is ligated to the DNA sequence 3'-proximal to the cutting site of HuIFN-α1, to create a fusion of the two genes while preserving the translational reading frame of both genes.

Since there are several HinfI sites in the coding regions of both HuIFN-α1 and HuIFN-β1 it is not possible to carry out a straightforward exchange of DNA sequences. Thus the procedures of Example I were followed for the isolation of the 217 bp fragment (denoted as β-A) as shown in FIG. 7.

In the case of HuIFN-α1, pGW5 was digested with HindIII and PvuII and two fragments were purified. One of the fragments is 278 bp in length (the small fragment) and contains two HinfI sites. This fragment is digested partially with HinfI to obtain two fragments, a 213 bp HindIII-HinfI fragment (α-A) and a 65 bp HinfI-PvuII fragment (α-B) (FIG. 8). The other HindIII-PvuII fragment containing the carboxy terminus coding region of HuIFN-α1 (α-C fragment) is saved for use as vector for cloning the hybrid.

Vector Preparation and Selection

Figure 12:
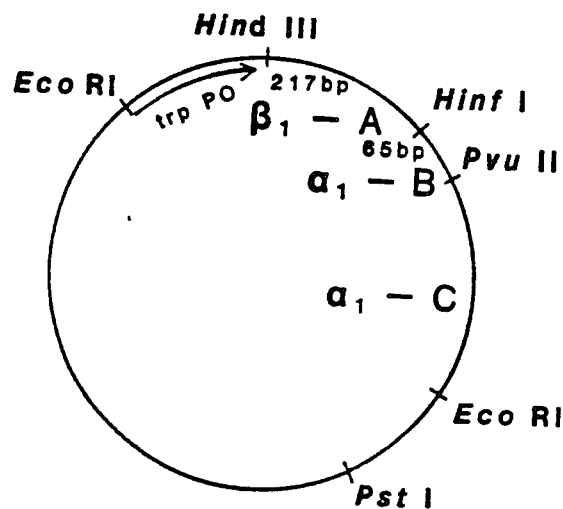
FIG. 12 illustrates the structure of the plasmid coding for the hybrid protein of Example II, infra.

The hybrid can be constructed by ligating O fragments β-A, α-B and α-C together as shown in FIG. 12. This ligated DNA was then used to transform competent E.coli cells. Transformants were plated onto broth plates containing 50 μg/ml of ampicillin and incubated at 37° C. Ampicillin resistant colonies were grown up in rich medium in the presence of 50 μg/ml of ampicillin and plasmid DNA isolated from each individual clone.

Figure 13:
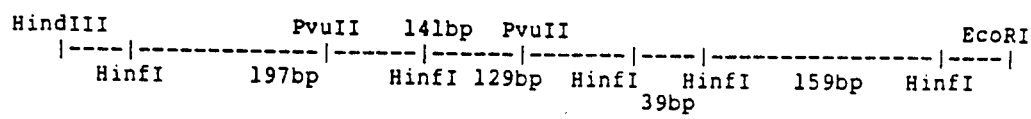
FIG. 13 illustrates the structure of the coding region of the hybrid gene incorporated in the plasmid of FIG. 12.

The gene structure of the desired hybrid clone is shown in FIG. 13. Therefore, the correct hybrid clone could be identified by digesting the plasmid DNA with the restriction enzyme PvuII and screening for the presence of the characteristic 141 bp PvuII fragment (FIG. 13) on 5% polyacrylamide gel. To further characterize the hybrid clone, the plasmid DNA was digested with HinfI and screened for the presence of the 197 bp, 159 bp, 129 bp, and 39 bp HinfI restriction fragments. By following this scheme, a number of hybrid clones were identified, one of which (denoted pDM101/trp/hybrid 1) was selected for further characterization and culturing to produce the hybrid interferon.

The nucleotide sequence of the region coding for the hybrid protein is shown in FIG. 14. Also shown in FIG. 14 is the amino acid sequence of the hybrid protein. This hybrid interferon is denoted HuIFN-β1α1 Hybrid 1 herein. The amino terminal portion of this polypeptide starting with methionine is composed of the amino acid sequence 1-73 of HuIFN-β1 and the carboxy terminal portion is composed of amino acids 74-166 of HuIFN-α1.

Biological Testing of HuIFN-β1α1 Hybrid 1

The assays used to determine interferon activities were identical to those used in Example I. The following Tables III and IV report the results of the cell growth regulatory assays and the natural killer cell activity assay.

TABLE III

| HuIFN | U/ml or *dilution of Extract | Percent Inhibition of Growth Cell Lines | |
|---|---|---|---|
| | | Daudi | HS294T Clone 6 |
| α¹ | 100 | 70 | 0 |
| | 500 | 80 | 9 |
| β¹ | 100 | 68 | 43 |
| | 500 | 72 | 80 |
| Hybrid of Example II | *1:2000 | 80 | 16 |
| | *1:20,000 | 23 | 28 |

Note:
Percent inhibition of growth by negative control (pDM101/trp) was included in the calculations to obtain the numbers shown above.

As reported and in contrast to Example I, the hybrid interferon of Example II inhibited the growth of both Daudi and HS294T Clone 6 cells, thus behaving like HuIFN-β1. Therefore, HuIFN-β1α1 Hybrid 1 supports the hypothesis expressed in Example I that the amino terminal portion of the interferon carries the determinat which governs cell specificity.

TABLE IV

| ACTIVATION OF NATURAL KILLER CELLS | | |
|---|---|---|
| HuIFN | U/ml or *dilution of Extract | Percent Killing (%) |
| α¹ | 100 | 39 |
| | 10 | 29 |
| β¹ | 100 | 38 |
| | 10 | 2 |
| Hybrid of Example II | *1:000 | 14 |
| Controls: | | |
| pDM101/trp | *1:000 | 10 |
| Cell Control (Spontaneous release of label) | | 7 |

Antiviral assays were carried out using the HuIFN-β1α1 Hybrid 1. Within the realm of sensitivity of the CPE inhbition assay no antiviral activity in the bacterial extracts containing the hybrid interferon was detected.

EXAMPLE III

Construction of HuIFN-α61Aβ1 Hybrid

This example describes the construction of a hybrid interferon containing sequences from HuIFN-α61A and HuIFN-β1. It involves the fusion of the amino acid terminal coding region of the HuIFN-α61A DNA to the DNA coding for the carboxy terminal region of HuIFN-β1 in such a way that the translational reading frame of the two genes are preserved and the resulting protein being expressed from this hybrid gene will have the amino acid sequence of HuIFN-α61A at its amino terminus and the amino acid sequence of HuIFN-β1 at its carboxy terminus.

Purification and Isolation of HuIFN-α61A and HuIFN-β1 DNA Sequences

The plasmids used in the construction of HuIFN-α61Aβ1 hybrid are plasmids pα61A and pDM101/trp/β1 Example I and FIG. 4).

Preparation of plasmid pα61A

In order to assemble the plasmid pα61A, the Namalwa cell human IFN enriched mRNA was used to construct complementary DNA (cDNA) clones in *E. coli* by the G/C tailing method using the PstI site of the cloning vector pBR322 (Bolivar, F., et al, *Gene*, 2:95-113 (1977)). A population of transformants containing approximately 50,000 individual cDNA clones was grown in one liter of medium overnight and the total plasmid DNA was isolated.

The sequences of two IFN-α clones (IFN-α1 and IFN-α2) have been published (Streuli, M., et al, *Science*, 209:1343-1347 (1980)). Examination of the DNA sequences of these two clones revealed that the restriction enzyme XhoII would excise a 260 bp fragment from either the IFN-α1 or the IFN-α2 gene (see FIG. 1). XhoII was prepared in accordance with the process described by Gingeras, T. R., and Roberts, R. J., *J Mol Biol*, 118:113-122 (1978).

One mg of the purified total plasmid DNA preparation was digested with XhoII and the DNA fragments were separated on a preparative 6% polyacrylamide gel. DNA from the region of the gel corresponding to 260 bp was recovered by electroelution and recloned by ligation into the BamHI site of the single strand bacteriophage m13:mp7. Thirty-six clones were picked at random, the single stranded DNA isolated therefrom, and the DNA was sequenced. The DNA sequences of four of these clones were homologous to known IFN-α DNA sequences. Clone mp7:α-260, with a DNA sequence identical to IFN-α1 DNA (Streuli, M. et al, *Science*, 209:1343-1347 (1980)) was chosen as a highly specific hybridization probe for identifying additional IFN-α DNA sequences. This clone is hereinafter referred to as the "260 probe."

In order to isolate other IFN-α gene sequences, a $^{32}$P-labelled 260 probe was used to screen a library of human genomic DNA by in situ hybridization. The human gene bank, prepared by Lawn, R. M., et al, *Cell*, 15:1157-1174 (1978), was generated by partial cleavage of fetal human DNA with HaeIII and AluI and cloned into bacteriophage λ Charon 4A with synthetic EcoRI linkers. Approximately 800,000 clones were screened, of which about 160 hybridized with the 260 probe. Each of the 160 clones was further characterized by restriction enzyme mapping and comparison with the published restriction maps of 10 chromosomal IFN genes (Nagata, S., et al, *J Interferon Research*, 1:333-336 (1981)). One of the clones, hybrid phage λ4A:α61 containing a 18 kb insert, was characterized as follows. A DNA preparation of λ4A:α61 was cleaved with HindIII, BglII, and EcoRI respectively, the fragments separated on an agarose gel, transferred to a nitrocellulose filter (Southern, E. M., *J Mol Biol*, 98:503-517 (1977)) and hybridized with 32P-labelled 260 probe. This procedure localized the IFN-α61 gene to a 1.9 kb BglII restriction fragment which was then isolated and recloned, in both orientations, by ligation of the fragment into BamHI cleaved m13:mp7. The two subclones are designated mp7:α61-1 and mp7:α61-2. The -1 designation indicates that the single-stranded bacteriophage contains insert DNA complementary to the mRNA (the minus strand) and the -2 designation indicates that the insert DNA is the same sequence as the mRNA (the plus strand).

The Sanger dideoxy-technique was used to determine the DNA sequence of the HuIFN-α61A gene. The DNA sequence of the IFN-α61A gene and the amino acid sequence predicted therefrom differ substantially from the other known IFN-α DNA and IFN-α amino acid sequences. In this regard Goeddel, D.V., et al *Nature* (1981) 290:20-26 discloses the DNA sequence of a partial IFN cDNA clone, designated LeIF-G. The sequence of the partial clone is similar to the 3'-end of the IFN-α61A DNA sequence, except for a nucleotide change in the codon for amino acid 128. As compared to the partial clone the IFN-α61A gene contains additional DNA that codes for the first 33 amino acids of IFN-α61A.

Assembly of the pα61A plasmid involved replacing the DNA fragment encoding the 23 amino acid signal polypeptide of preinterferon with a 120 bp EcoRI/-Sau3A promoter fragment *E.coli* trp promoter, operator, and trp leader ribosome binding site preceoperator, ding an ATG initiation codon and using HindIII site that was inserted, 59 nucleotides 3'- of the TGA translational stop codon, to insert the gene into the plasmid pBW11 (a derivative of pBR322 having a deletion between the HindIII and PvuII sites). The complete DNA sequence of the promoter and gene fragments inserted between the EcoRI and HindIII sites of pBW11 is shown in FIG. 16 which also shows the exact location of relevant cloning sites. Details of the construction are described below.

The coding region for mature IFN-α61 has three Sau3A sites, one of which is between codons for amino acids 2 and 3. A synthetic HindIII site was inserted 59 nucleotides 3'- of the coding region and the resulting construct was subjected to a HindIII/partial Sau3A digest. A 560 bp fragment was isolated from the digest. This fragment and a 120 bp EcoRI to Sau3A *E.coli* promoter fragment were ligated together in a +three way directed ligation into the EcoRI to HindIII site of pBW11. The promoter fragment, contained a synthetic HindIII restriction site, ATG inititation codon, the initial cysteine codon (TGT) common to all known IFN-αs, and a Sau3A "sticky end". The ligation mixture was used to transform *E.coli*. The final expression plasmid obtained, pα61A, is shown in FIG. 15.

As in Examples I and II, the hybrid gene of the example was constructed by taking advantage of the homologies between HuIFN-α61A (the DNA sequence of the HuIFN-α61A gene and the amino acid sequence it encodes are shown in FIG. 16) and HuIFN-β1 at around amino acid 40 of both proteins (FIG. 17). The DNA sequence 5'-proximal to the DdeI restriction enzyme cutting site of the HuIFN-α61A DNA (the arrow in FIG. 17 depicts the cutting site), is ligated to the DNA sequence 3'-proximal to the cutting site of HuIFN-β1, to create a fusion of the two genes while preserving the translational reading frame of both genes.

Since there are several DdeI sites in the coding regions of both HuIFN-α61A and HuIFN-β1, and the DdeI cohesive ends are not identical, therefore, it is not possible to carry out a straightforward exchange of DNA fragments. Thus variations of the procedures described in Examples I and II were used.

In the case of HuIFN-α61A, pα61A was digested with EcoRI and PvuII and the 387 bp fragment containing three DdeI sites was purified. This fragment was digested partially with DdeI, the cohesive ends repaired to a blunt end by the action of DNA Polymerase I Klenow fragment as described by Maniatis et al., ("Molecular Cloning" Cold Spring Harbor Laboratory, Cold Spring Harbor, N.Y. p. 113-114 (1982)). The repaired DNA fragments were then digested with HindIII and the 120 bp fragment (denoted as Alpha) purified from an acrylamide gel (FIG. 18).

In the case of HuIFN-β1, pDM101/trp/β1 was digested with EcoRI and BamHI and the smaller fragment, containing the interferon gene purified (FIG. 4). This fragment was partially digested with DdeI, the cohesive ends removed by treatment with S1 nuclease as described by Maniatis et al., ("Molecular Cloning", Cold Spring Harbor Laboratory, Cold Spring Harbor, N.Y. p. 140 and 237-238 (1982)). The S1 nuclease treated DNA was then digested with BglII and the 381 bp fragment (denoted as Beta) purified (FIG. 19).

Vector preparation

Figure 20:
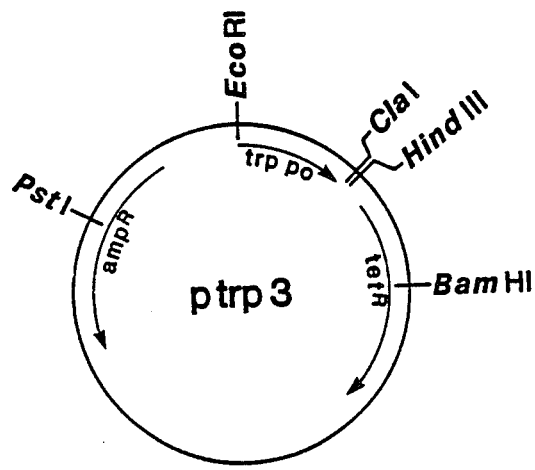
FIG. 20 illustrates the structure of a plasmid ptrp3 used in the methodology of the invention.

The plasmid ptrp3 (FIG. 20) is a derivative of pBR322, with the EcoRI - ClaI region replaced by the E.coli trp promoter sequence. This plasmid was digested with HindIII and BamHI and the large plasmid fragment containing the E.coli trp promoter was purified (FIG. 20).

Figure 21:
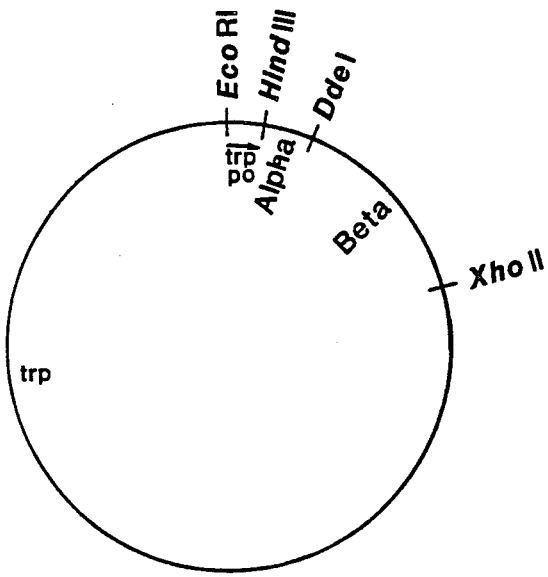
FIG. 21 illustrates the structure of the plasmid coding for the hybrid protein of Example III infra.

The hybrid was constructed by ligating this vector fragment to the Alpha and Beta fragments as shown in FIG. 21. This ligated DNA was transformed into competent E.coli cells and plated on plates containing ampicillin. Resistant colonies were grown up individually in rich medium and plasmid DNA isolated from them. The plasmid DNA were digested with DdeI and screened on acrylamide gels for the presence of the 91 bp and 329 bp DdeI fragments characteristic of the hybrid as shown in FIG. 22. A number of hybrid clones were identified, one of which (denoted as pαβ62) was selected for further characterization and culturing to produce the hybrid interferon.

The nucleotide sequence of the region coding for the hybrid protein is shown in FIG. 23. Also shown in FIG. 23 is the amino acid sequence of the hybrid protein. This hybrid interferon is denoted 25 HuIFN-α61Aβ1 herein. The amino terminal portion of this polypeptide starting with methionine is composed of the amino acid sequence 1-41 of HuIFN-α61A and the carboxy terminal portion is composed of amino acids 47-166 of HuIFN-β1.

Biological Testing of HuIFN-α61Aβ1 Hybrid

The assays used to determine interferon activities were identical to those used in Examples I and II. However, an additional assay was incorporated, the protein kinase phosphorylation assay, to confirm the change we observed in host range specificity of the antiviral activity of this hybrid as compared to its parents.

Growth Inhibition and Natural Killer Cell Assays

No inhibition of either Daudi or Clone 6 cells was exhibited. Similarly no activation of natural killer cells was detected.

Antiviral Assays

We performed our biological antiviral assays as described for Examples I and II on two different cell lines: the human trisomic 21 cell line (GM2504), and the bovine MDBK line, with vesicular stomatitis virus as the challenge virus. Our results are summarized in Table V. As compared to the previous two examples, HuIFN-α61Aβ1 had antiviral activity on bovine cells ($\sim 10^3$ U/ml), but no detectable antiviral activity on human GM2504 cells.

69K Protein Phosphorylation

Figure 24:
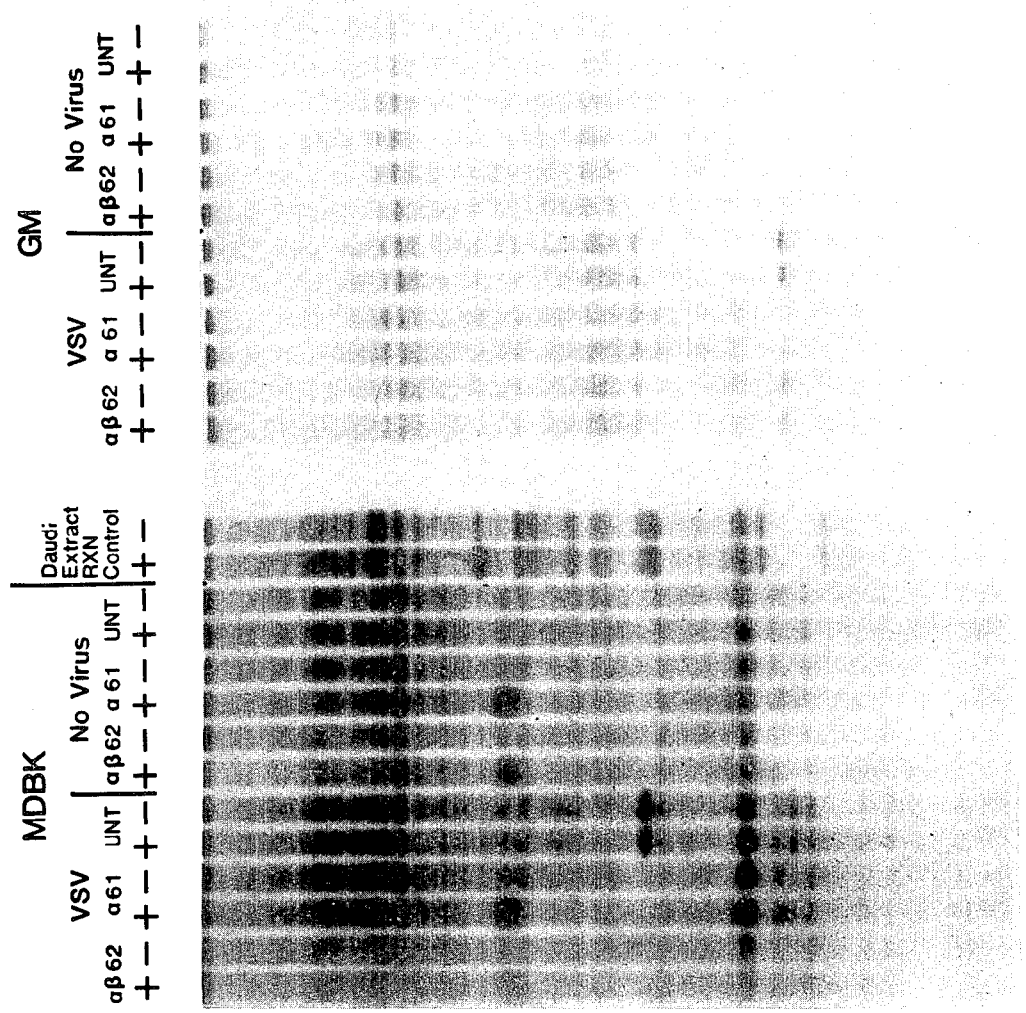
FIG. 24 depicts a protein gel showing the phosphorylation of the protein kinase in bovine cells.

The biological activity of interferons has usually been studied by infecting treated cell cultures and measuring the inhibition of virus replication. A more direct approach would be to measure, in the cells, some interferon-induced biochemical changes associated with the establishment of the antiviral state. One of the clearest biochemical alterations observed after interferon treatment is an impairment of viral protein synthesis (M. Revel, "Interferon-Induced Translational Regulation," Texas Rep Biol Med 35:212-219 (1977)). Several cellular inhibitions of mRNA translation have been identified in interferonm-treated cells and shown, after purification, to be enzymes that act on various components of the mRNA translation machinery. One cellular enzyme is a specific protein kinase, phosphorylating a 69,000 Mr polypeptide ($P_1$) and the small subunit of eukaryotic initiation factor 2 (eIF-2). (For review, see C. Samuel, "Procedures for Measurement of Phosphorylation of Ribosome Associated Proteins in Interferon Treated Cells." Methods in Enzymology, 79:168-178. (1981)). Phosphorylation of protein $P_1$ is considered one of the most sensitive biochemical markers of interferon action and is significantly enhanced in interferon-treated cells as compared to untreated cells. To confirm the change in the host range in the antiviral activity of HuIFN-α61Aβ1, we used the protein kinase phosphorylation assay as has been described by A. Kimchi et al, "Kinetics of the Induction of Three Translation-Regulatory Enzymes by Interferon", Proc Natl Acad Sci, 76:3208-3212 (1979). We have found that the HuIFN-α61Aβ1 indicated in FIG. 24 as αβ62, induced the phosphorylation of the kinase in the bovine MDBK cells and not in the human GM2504 cells. The + and − symbols in FIG. 24 indicate the presence or absence of polyIC double stranded RNA in the reaction. The arrow points to the bands indicating the interferon-induced phosphorylation of the 69K double stranded RNA dependent cellular protein ($P_1$). These results confirm the antiviral activity of HuIFN-α61Aβ1 on bovine cells.

TABLE V

Antiviral activity of recombinant parent and hybrid interferons on bovine and human cells in culture

| | Cell Line | |
|---|---|---|
| | Human Fibroblasts (GM2504) | Bovine Fibroblasts (MDBK) |
| IFN/type | IFN Titer (U/ml) | |
| IFN-α61A | >$10^6$ | $10^6$ |
| IFN-β1 | 5 × $10^5$ | 5 × $10^3$ |
| IFN-α61Aβ1 | <30 | $10^3$ |
| trp control | <30 | <30 |

The cell growth regulating activity exhibited by certain α-β hybrid interferons makes these hybrids potentially useful for treating tumors and cancers such as osteogenic sarcoma, multiple myeloma, Hodgkin's disease, nodular, poorly differentiated lymphoma, acute lymphocytic leukemia, breast carcinoma, melanoma, and nasopharyngeal carcinoma. Because of their restricted activity such treatment is not expected to be associated with side effects such as immunosuppression that often is observed with conventional non-hybrid interferon therapy. Also it is - expected that the α-β hybrid interferons exhibiting interferon activity restricted to antiviral activity may be used to treat viral infections with a potential for interferon therapy such as encephalomyocarditis virus infection, influenza and other respiratory tract virus infections, rabies and other viral zoonoses and arbovirus infections.

Pharmaceutical compositions that contain a hybrid interferon as an active ingredient will normally be formulated with an appropriate solid or liquid carrier depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solid, eg tablet or capsule, or liquid solutions or suspensions. The hybrid interferon will usually be formulated as a unit dosage form that contains approximately 100 µg of protein per dose.

The hybrid interferons of the invention may be administered to humans or other animals on whose cells they are effective in various manners such as orally, intravenously, intramuscularly, intraperitoneally, intranasally, intradermally, and subcutaneously. The particular mode of administration and dosage regimen will be selected by the attending physician taking into account the particulars of the patient, the disease and the disease state involved. For instance, viral infections are usually treated by daily or twice daily doses over a few days to a few weeks; whereas tumor or cancer treatment typically involves daily or multidaily doses over months or years. The same dose levels as are used in conventional nonhybrid interferon therapy may be used. A hybrid interferon may be combined with other treatments and may be combined with or used in association with other chemotherapeutic or chemopreventive agents for providing therapy against neoplasms or other conditions against which it is effective.

Modifications of the above described modes for carrying out the invention, such as, without limitation, use of alternative vectors, alternative expression control systems in the vector, and alternative host microorganisms and other therapeutic or related uses of the hybrid interferons, that are obvious to those of ordinary skill in the biotechnology, pharmaceutical, medical and/or related fields are intended to be within the scope of the following claims.

We claim:

1. A multiclass hybrid interferon polypeptide having an amino acid sequence composed of two distinct amino acid subsequences one of which subsequences comprises the amino acid sequence 1–73 of the amino terminal enc of HuIFN-α1, and the other of which subsequences comprises the amino acid sequence 74–166 of the carboxy terminal end of HuIFN-β1.

2. A multiclass hybrid interferon polypeptide having an amino acid sequence composed of two distinct amino acid subsequences one of which subsequences comprises the amino acid sequence 1–41 of the amino terminal enc of HuIFN-α61A, and the other of which subsequences comprises the amino acid sequence 47–166 of the carboxy terminal end of HuIFN-β1.

3. A multiclass hybrid interferon polypeptide having an amino acid sequence composed of two distinct amino acid subsequences one of which subsequences comprises the amino acid sequence 1–73 of the amino terminal eno of HuIFN-β1, and the other of which subsequences comprises the amino acid sequence 74–167 of the carboxy terminal end of HuIFN-α1.

4. A pharmaceutical composition comprising a cell growth regulating or viral inhibiting effective amount of the multiclass hybrid interferon polypeptide of claim 1 admixed with a pharmaceutically acceptable vehicle or carrier.

5. A pharmaceutical composition comprising a cell growth regulating or viral inhibiting effective amount of the multiclass hybrid interferon polypeptide of claim 2 admixed with a pharmaceutically acceptable vehicle or carrier.

6. A pharmaceutical composition comprising a cell growth regulating or viral inhibiting effective amount of the multiclass hybrid interferon polypeptide of claim 3 admixed with a pharmaceutically acceptable vehicle or carrier.

7. A method of regulating cell growth in an animal patient comprising administering to said patient a cell growth regulating amount of the multiclass hybrid interferon polypeptide of claim 1.

8. A method of regulating cell growth in a human or other animal patient comprising administering to said patient a cell growth regulating amount of the multiclass hybrid interferon polypeptide of claim 3.

9. A method of treating an animal patient for a viral disease comprising administering to the patient a viral disease inhibiting amount of the multiclass hybrid interferon polypeptide of claim 2.

* * * * *